United States Patent [19]

Olson

[11] Patent Number: 4,967,595

[45] Date of Patent: Nov. 6, 1990

[54] AVIATION FUEL SAMPLE TESTER

[76] Inventor: Roger Olson, 313 George Ave., Amery, Wis. 54001

[21] Appl. No.: 341,913

[22] Filed: Apr. 24, 1989

[51] Int. Cl.$^5$ .............................................. G01N 9/10
[52] U.S. Cl. .................................. 73/440; 73/864.51; 73/863.86
[58] Field of Search ............... 73/440, 863.86, 864.51, 73/61.1 R, 311; 116/228

[56] References Cited

U.S. PATENT DOCUMENTS

| | | | |
|---|---|---|---|
| 1,344,663 | 6/1920 | Waldrep | 73/311 |
| 1,697,353 | 1/1929 | Garrison | 73/440 |
| 3,011,349 | 12/1961 | Kratz | 73/863.86 |
| 3,198,016 | 8/1965 | Poorman | 73/863.86 |
| 3,386,289 | 6/1968 | Norcross | 73/440 |
| 3,451,273 | 6/1969 | Ludlow | 73/440 |
| 3,626,763 | 12/1971 | White | 73/440 |
| 3,631,727 | 1/1972 | White | 73/440 |
| 4,103,700 | 8/1978 | Orrell et al. | 73/440 |
| 4,126,044 | 11/1978 | Tichy et al. | 73/440 |
| 4,142,419 | 3/1979 | Fenne et al. | 73/440 |
| 4,649,747 | 3/1987 | Barber et al. | 73/440 |
| 4,700,580 | 10/1987 | Kamin | 73/61.1 R |
| 4,702,109 | 10/1987 | Viola | 73/440 |

Primary Examiner—John Chapman
Attorney, Agent, or Firm—Peterson, Wicks, Nemer & Kamrath

[57] ABSTRACT

A device (10) for testing samples of aviation fuel drained through a drain valve of an aircraft fuel system is disclosed including a pin (22) upstanding from the bottom (18) and extending concentrically with the sidewall (16) out of and above the inlet (20) of a container (12). Thus, the fuel draining from the drain valve is caught and collected by the inlet (20) and is contained in the container (12) for visual observation for particulate contamination and liquid separation. Device (10) further includes specific gravity floats (32, 34) having densities to float in water but not in jet fuel and gasoline and to float in water and jet fuel but not in gasoline, respectively. Thus, by observing the condition of the floats (32, 34), the pilot can quickly, accurately, and clearly determine whether the sample is gasoline, jet fuel, or water. Device (10) further includes a screen (36) anchored to the sidewall (16) of the container (12) adjacent the inlet (20) for preventing passage of the floats (32, 34) from the container (12) through the inlet (20) while permitting generally unrestricted flow of liquid into the container (12) through the inlet (20). In the most preferred form, pin (22) upstands from the bottom (18) of the container (12) and passes through a central aperture (40) formed in the screen (36).

16 Claims, 1 Drawing Sheet

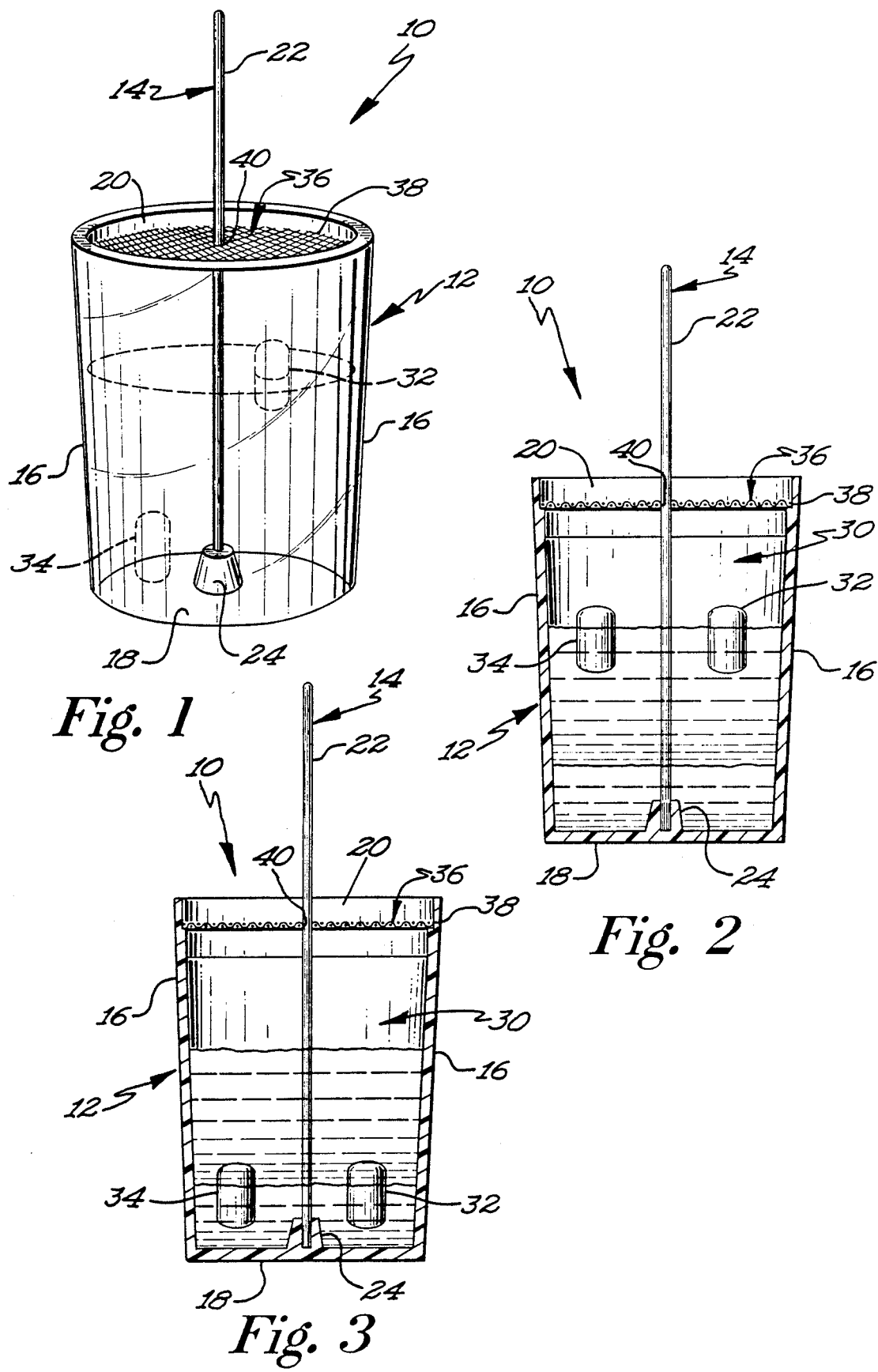

4,967,595

AVIATION FUEL SAMPLE TESTER

BACKGROUND

The present invention generally relates to a device for testing samples of aviation fuel for contaminants.

The main reason for light airplane engine failure is fuel contamination. This contamination is usually caused by either water in the fuel or improper fuel being put on board the aircraft. Fuel should be checked by the pilot during pre-flight and after each refueling for contaminants and for correct octane. The present method of testing is to drain a small amount of liquid from the lowest point in the fuel cell and/or the lowest point in the system into a clear container. The containers typically include a pin for opening fuel drain valves provided in the fuel system of the aircraft, with the container catching and holding the fuel released through the fuel drain valve when opened by the pin. The container typically holds only a few ounces of liquid. The standard fuel testing technique is to look for water bubbles or improper color of the fuel sample held in the container.

However, problems are encountered in the ability of the pilot to accurately determine whether or not fuel contamination has in fact occurred. For example, if the water present in the fuel system is greater than a few ounces, the sample held in the container could be all water. Due to the similar colors of water and fuel, it is difficult for the pilot to see any difference between a sample container holding all water or all fuel, especially when the testing is being performed at night. Thus, the pilot could easily believe that a sample including all water is all fuel and thus incorrectly diagnose a contaminated sample.

Similarly, it is difficult for the pilot to see any differences between a container holding samples of different types of aviation fuel. Thus, it is difficult for a pilot to determine whether a gasoline powered aircraft has been misfueled with jet fuel or vice versa.

Accident reports verify that a need exists for a better method for pilots to test samples of aviation fuel in addition to the visual fuel checks currently utilized.

SUMMARY

The present invention solves this need and other problems in the field of aviation fuel contamination determination by providing, in the most preferred form, a device for testing samples drained from a drain valve of an aircraft fuel system. Specifically, the device includes a member for opening the drain valve which extends above the inlet of a container which catches and collects the fuel draining from the opened drain valve. A specific gravity float is located and freely moveable within the container and is prevented from passing through the inlet of the container by a member located adjacent the inlet which does not generally restrict flow of the fuel draining from the drain valve into the container through the inlet.

It is thus an object of the present invention to provide a novel device for testing samples of aviation fuel.

It is further an object of the present invention to provide such a novel aviation fuel sample tester for testing samples drained from a drain valve of an aircraft fuel system.

It is further an object of the present invention to provide such a novel aviation fuel sample tester allowing visual observation for particulate contamination and/or liquid separation.

It is further an object of the present invention to provide such a novel aviation fuel sample tester allowing visual determination of the type of liquid in the drained sample.

It is further an object of the present invention to provide such a novel aviation fuel sample tester providing clear and concise reading.

It is further an object of the present invention to provide such a novel aviation fuel sample tester operable in any light condition.

It is further an object of the present invention to provide such a novel aviation fuel sample tester having very trouble free operation.

It is further an object of the present invention to provide such a novel aviation fuel sample tester which is not susceptible to wear.

It is further an object of the present invention to provide such a novel aviation fuel sample tester not requiring pilot calibration or meter or gauge reading by the pilot.

It is further an object of the present invention to provide such a novel aviation fuel sample tester which greatly reduces engine failure resulting from aircraft misfueling.

These and further objects and advantages of the present invention will become clearer in light of the following detailed description of an illustrative embodiment of this invention described in connection with the drawings.

DESCRIPTION OF THE DRAWINGS

The illustrative embodiment may best be described by reference to the accompanying drawings where:

FIG. 1 shows a perspective view of a device for testing samples of aviation fuel drained from a drain valve of an aircraft according to the preferred teachings of the present invention.

FIGS. 2 and 3 show cross sectional side views of the device of FIG. 1.

All FIGURES are drawn for ease of explanation of the basic teachings of the present invention only; the extensions of the FIGURES with respect to number, position, relationship, and dimensions of the parts to form the preferred embodiment will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

Where used in the various FIGURES of the drawings, the same numerals designate the same or similar parts. Furthermore, when the terms "top", "bottom", "first", "second", "sidewall", "inside", and similar terms are used herein, it should be understood that these terms have reference only to the structure shown in the drawings as it would appear to a person viewing the drawings and are utilized only to facilitate describing the invention.

DESCRIPTION

A device for testing samples of aviation fuel for contamination is shown in the drawings and generally designated 10. Device 10 generally includes a sample container 12 for holding a sample of aviation fuel. Container 12 should be formed of clear or transparent material such as plastic or glass which allows visual observation of the fuel sample located in container 12. Container 12 includes means 14 for opening drain valves of aircraft, not shown. Means 14 must be arranged such that fuel drained through the drain valve is caught, collected and held by container 12.

It can be appreciated that container 12 and means 14 can be of a variety of forms and types. For example, in the preferred form shown in the drawings, container 12 is generally beaker shaped and includes a cylindrical sidewall 16, a closed, circular bottom 18, and an open, circular top or inlet 20. Means 14 is a pin 22 which upstands from an upstanding boss 24 integrally formed with bottom 18, with pin 22 located concentrically within sidewall 16 along the diameter thereof and extending above and beyond top 20. Pin 22 in the preferred form is formed by a metallic rod having its lower end anchored in boss 24 by injection molding container 12 with pin 22 in place. As indicated, container 12 may have other shapes including test tube configurations and/or funnel configurations, and bottom 18 may have provisions to allow drainage from container 12 into a large container. Additionally, container 12 may include other accessories helpful in fuel sampling and/or preflight reviews such as but not limited to provisions for removably mounting a slotted/Phillips blade screwdriver. Similarly, means 14 may have other forms including a plastic pin upstanding from a spider which in turn lodges and/or wedges in the sidewall of container 12 spaced from the bottom of container 12. Specifically, means 14 may be adaptable for opening quick drain valves presently utilized in aircraft including regular, flush mount, recessed, or bayonet types.

Device 10 further includes provision 30 for indicating the specific gravity of the fuel sample located in container 12. Specifically, in the most preferred form, provision 30 is shown as a plurality of floats 32 and 34 of varying densities to float and sink in liquids of different specific gravities, with floats 32 and 34 having diameters which are substantially smaller than the size of container 12 and open top 20 thereof to allow floats 32 and 34 to be freely moveable in container 12 and to prevent floats 32 and 34 from wedging in container 12. Provision 30 further includes means 36 for preventing passage of floats 32 and 34 through open top 20 while permitting generally unrestricted flow of liquid through open top 20 into container 12. Thus, the fuel sample may be poured from container 12 through open top 20 without fear of floats 32 and 34 being poured or falling from container 12 with the sample. In the preferred form, means 36 is a screen having its outer circumference 38 anchored to the inside surface of sidewall 16 of container 12 adjacent inlet 20. In the most preferred form, screen 36 includes a central aperture 40 of a size allowing pin 22 to extend therethrough but preventing passage of floats 32 and 34 therethrough when pin 22 extends therethrough.

In the preferred form, float 32 has a density to float in liquids having a specific gravity of greater than 0.71 and float 34 has a density to float in liquids having a specific gravity of greater than 0.82. Thus, as water has a specific gravity of 1.0, both floats 32 and 34 will float in a manner as shown in FIG. 2 if water is present in container 12. Additionally, as jet fuel such as kerosene has a specific gravity of 0.82, float 32 will float and float 34 will not float in a manner as shown in FIG. 1 if jet fuel is present in container 12. Similarly, as gasoline has a specific gravity of 0.71, neither float 32 or 34 will float in a manner as shown in FIG. 3 if gasoline is present in container 12.

Now that the construction of device 10 according to the preferred teachings of the present invention has been set forth, the operation and subtle features of device 10 can be explained and appreciated. Specifically, a sample from the lowest point in the fuel cell and/or the lowest point in the fuel system of the aircraft is collected into container 12. In the most preferred form, the sample is drained by opening a drain valve by pushing pin 22 of container 12 into the drain valve. Fuel drained from the fuel system is caught and collected by inlet 20 of container 12. At that time, the sample should be visually observed through sidewall 16 and/or bottom 18 for signs of contamination. This could include signs of particulate contamination and/or separation of liquids being sampled. Also, the color of the sample should be viewed in a manner according to existing preflight reviews. However, in addition according to the teachings of the present invention, the condition identified by floats 32 and 34 can be viewed. Specifically, if both floats 32 and 34 are floating as illustrated in FIG. 2, the sample collected would be water, if one float is floating, in this case, float 32 as illustrated in FIG. 1, the sample collected would be jet fuel, and if neither float 32 and 34 was floating as illustrated in FIG. 3, the sample collected would be gasoline. Thus, the pilot can quickly identify whether the aircraft has been correctly fueled by jet fuel or gasoline, as the case may be.

It can then be appreciated that floats 32 and 34 may be colored to be visible through sidewall 16 and/or bottom 18 when located in a liquid in container 12. Thus, a clear and concise reading can be made by the pilot by simply looking at the position of floats 32 and 34, with the pilot not having to attempt to differentiate between color differentiations existing between samples of pure water, pure jet fuel, or pure gasoline. This feature of the present invention is especially important in low light circumstances such as preflight reviews occurring after dark.

It can further be appreciated that device 10 has a very trouble free operation as floats 32 and 34 are the only moving parts and are generally not susceptible to wear. Further, it is not necessary for the pilot to calibrate device 10 or to read a meter or gauge according to the teachings of the present invention. Thus, device 10 allows the pilot to make a rapid, clear and accurate determination of the content of the sample located in container 12 and without relying solely upon subtle color differences existing between potential liquids which may be found in aviation fuel systems.

It can be appreciated that container 12 may include indicia providing instructions for interpreting the position of floats 32 and 34 in determining whether the sample is water, gasoline, or jet fuel. Additionally, octane color codes may be further provided, if so desired.

Device 10 according to the teachings of the present invention will then prevent aircraft engine failure resulting from misfueling the aircraft with incorrect fuel which was previously difficult to detect by preflight reviews performed on the aircraft by the pilot.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. Device for testing samples drained from a drain valve of an aircraft fuel system comprising, in combination: means for opening the drain valve of the aircraft fuel system for draining fuel from the aircraft fuel system; a container having an inlet of a size to catch and collect fuel drained from the aircraft fuel system, with the container formed of transparent material to allow visual observation of the sample of aviation fuel contained in the container, with the drain valve opening means extending above the inlet of the container; a first specific gravity float located and freely moveable within the container, with the first specific gravity float having a density to float in liquids having a specific gravity of greater than 0.71; a second specific gravity float located and freely moveable within the container, with the second specific gravity float having a density to float in liquids having a specific gravity greater than 0.82; and means located adjacent the inlet of the container for preventing passage of the first and second specific gravity floats through the inlet of the container while permitting generally unrestricted flow of liquid into the container through the inlet, wherein if the first specific gravity float floats in the sample indicates that the sample in the container is jet fuel or water, wherein if the first specific gravity float does not float in the sample indicates that the sample in the container is gasoline, wherein if the second specific gravity float floats in the sample indicates that the sample in the container is water, and wherein if the second specific gravity float does not float in the sample indicates that the sample is gasoline or jet fuel.

2. The sample testing device of claim 1 wherein the opening means comprises a pin extending above the inlet of the container.

3. The sample testing device of claim 2 wherein the pin extends through the passage preventing means.

4. The sample testing device of claim 3 wherein the container is generally cylindrical in shape, with the container including a sidewall which is generally concentric with the pin and including a bottom, with the pin upstanding from the bottom.

5. The sample testing device of claim 4 wherein the passage preventing means comprises a screen anchored to the sidewall of the container, with the screen having a central aperture of a size allowing the pin to pass therethrough while preventing passage of the specific gravity floats therethrough.

6. Device for testing samples drained from a drain valve of an aircraft fuel system comprising, in combination: means for opening the drain valve of the aircraft fuel system for draining fuel from the aircraft fuel system; a container having an inlet of a size to catch and collect fuel drained from the aircraft fuel system, with the container being generally cylindrical in shape and formed of transparent material to allow visual observation of the sample of aviation fuel contained in the container, with the container including a sidewall, with the drain valve opening means extending above the inlet of the container; at least a first specific gravity float located and freely moveable within the container; and means located adjacent the inlet of the container for preventing passage of the specific gravity float through the inlet of the container while permitting generally unrestricted flow of liquid into the container through the inlet, wherein the passage preventing means comprises a screen anchored to the sidewall of the container.

7. The sample testing device of claim 6 wherein the opening means comprises a pin extending above the inlet of the container.

8. The sample testing device of claim 7 wherein the pin extends through the passage preventing means.

9. Device for testing samples drained from a drain valve of an aircraft fuel system comprising, in combination: means for opening the drain valve of the aircraft fuel system for draining fuel from the aircraft fuel system; a container having an inlet of a size to catch and collect fuel drained from the aircraft fuel system, with the container formed of transparent material to allow visual observation of the sample of aviation fuel contained in the container, with the drain valve opening means extending through the container and above the inlet of the container; at least a first specific gravity float located and freely moveable within the container; and means located adjacent the inlet of the container for preventing passage of the specific gravity float through the inlet of the container while permitting generally unrestricted flow of liquid into the container through the inlet, wherein the passage preventing means includes means for allowing the opening means to pass therethrough while preventing passage of the specific gravity float therethrough.

10. Device for testing samples drained from a drain valve on an aircraft fuel system comprising, in combination: means for opening the drain valve of the aircraft fuel system for draining fuel from the aircraft fuel system; a container having an inlet of a size to catch and collect fuel drained from the aircraft fuel system, with the container formed of transparent material to allow visual observation of the sample of aviation fuel contained in the container, with the drain valve opening means comprising a pin extending through the container and above the inlet of the container; at least a first specific gravity float located and freely moveable within the container; and means located adjacent the inlet of the container for preventing passage of the specific gravity float through the inlet of the container while permitting generally unrestricted flow of liquid into the container through the inlet, wherein the pin extends through the passage preventing means.

11. The sample testing device of claim 6 wherein the first specific gravity float is colored to be visible through the container when located in the sample of aircraft fuel contained in the container.

12. The sample testing device of claim 1 wherein the first and second specific gravity floats are colored to be visible through the container when located in the sample of aircraft fuel contained in the container.

13. The sample testing device of claim 9 wherein the first specific gravity float is colored to be visible through the container when located in the sample of aircraft fuel contained in the container.

14. The sample testing device of claim 6 wherein the first specific gravity float has a density to float in liquids having a specific gravity of greater than 0.71 to indicate that the sample in the container is jet fuel or water.

15. The sample testing device of claim 14 further comprising, in combination: a second specific gravity float located and freely moveable within the container, with the passage preventing means preventing passage of the second specific gravity float through the inlet of the container while permitting generally unrestricted flow of liquid into the container through the inlet.

16. The sample testing device of claim 15 wherein the second specific gravity float has a density to float in liquids having a specific gravity greater than 0.82 to indicate that the sample in the container is water.

* * * * *